United States Patent
Gravagna et al.

(10) Patent No.: US 9,750,846 B2
(45) Date of Patent: *Sep. 5, 2017

(54) BIORESORBABLE AND BIOCOMPATIBLE COMPOUNDS FOR SURGICAL USE

(75) Inventors: Philippe Gravagna, Irigny (FR); Yves Bayon, Lyons (FR); Sebastien Ladet, Lyons (FR)

(73) Assignee: Sofradim Production SAS, Trevoux (FR)

( * ) Notice: Subject to any disclaimer, the term of this patent is extended or adjusted under 35 U.S.C. 154(b) by 243 days.

This patent is subject to a terminal disclaimer.

(21) Appl. No.: 13/458,573

(22) Filed: Apr. 27, 2012

(65) Prior Publication Data

US 2012/0276161 A1    Nov. 1, 2012

Related U.S. Application Data

(63) Continuation of application No. 11/899,694, filed on Sep. 7, 2007, now abandoned.

(51) Int. Cl.
*A61L 27/20* (2006.01)
*A61L 27/24* (2006.01)

(52) U.S. Cl.
CPC .............. *A61L 27/20* (2013.01); *A61L 27/24* (2013.01)

(58) Field of Classification Search
None
See application file for complete search history.

(56) References Cited

U.S. PATENT DOCUMENTS

| | | |
|---|---|---|
| 4,400,833 A | 8/1983 | Kurland |
| 4,511,653 A | 4/1985 | Play et al. |
| 4,931,546 A | 6/1990 | Tardy et al. |
| 4,950,483 A | 8/1990 | Ksander et al. |
| 5,201,764 A | 4/1993 | Kelman et al. |
| 5,256,418 A | 10/1993 | Kemp et al. |
| 5,263,983 A | 11/1993 | Yoshizato et al. |
| 5,306,500 A | 4/1994 | Rhee et al. |
| 5,328,955 A | 7/1994 | Rhee et al. |
| 5,350,583 A | 9/1994 | Yoshizato et al. |
| 5,376,375 A | 12/1994 | Rhee et al. |
| 5,399,361 A | 3/1995 | Song et al. |
| 5,413,791 A | 5/1995 | Rhee et al. |
| 5,510,418 A * | 4/1996 | Rhee et al. .......... 525/54.2 |
| 5,536,656 A | 7/1996 | Kemp et al. |
| 5,565,210 A | 10/1996 | Rosenthal et al. |
| 5,618,551 A | 4/1997 | Tardy et al. |
| 5,681,568 A | 10/1997 | Goldin et al. |
| 5,686,115 A | 11/1997 | Vournakis et al. |
| 5,709,934 A | 1/1998 | Bell et al. |
| 5,766,631 A | 6/1998 | Arnold |
| 5,785,983 A | 7/1998 | Furlan et al. |
| 5,800,541 A | 9/1998 | Rhee et al. |
| 5,861,034 A | 1/1999 | Taira et al. |
| 5,863,984 A | 1/1999 | Doillon et al. |
| 5,871,767 A | 2/1999 | Dionne et al. |
| 5,876,444 A | 3/1999 | Lai |
| 5,962,136 A | 10/1999 | Dewez et al. |
| 5,993,844 A | 11/1999 | Abraham et al. |
| 5,997,895 A | 12/1999 | Narotam et al. |
| 6,083,522 A | 7/2000 | Chu et al. |
| 6,165,488 A | 12/2000 | Tardy et al. |
| 6,197,935 B1 | 3/2001 | Doillon et al. |
| 6,221,109 B1 | 4/2001 | Geistlich et al. |
| 6,264,702 B1 | 7/2001 | Ory et al. |
| 6,312,474 B1 | 11/2001 | Francis et al. |
| 6,391,333 B1 | 5/2002 | Li et al. |
| 6,391,939 B2 | 5/2002 | Tayot et al. |
| 6,410,044 B1 | 6/2002 | Chudzik et al. |
| 6,440,167 B2 | 8/2002 | Shimizu |
| 6,454,787 B1 | 9/2002 | Maddalo et al. |
| 6,500,464 B2 | 12/2002 | Ceres et al. |
| 6,509,031 B1 | 1/2003 | Miller et al. |
| 6,514,286 B1 | 2/2003 | Leatherbury et al. |
| 6,596,304 B1 | 7/2003 | Bayon et al. |
| 6,599,524 B2 | 7/2003 | Li et al. |
| 6,599,690 B1 | 7/2003 | Abraham et al. |
| 6,652,594 B2 | 11/2003 | Francis et al. |
| 6,682,760 B2 | 1/2004 | Noff et al. |
| 6,706,684 B1 | 3/2004 | Bayon et al. |
| 6,730,299 B1 | 5/2004 | Tayot et al. |
| 6,743,435 B2 | 6/2004 | DeVore et al. |
| 6,773,723 B1 | 8/2004 | Spiro et al. |
| 6,790,454 B1 | 9/2004 | Abdul Malak et al. |
| 6,893,653 B2 | 5/2005 | Abraham et al. |
| 6,949,625 B2 | 9/2005 | Tayot |
| 6,974,862 B2 | 12/2005 | Ringeisen et al. |
| 6,977,231 B1 | 12/2005 | Matsuda |
| 7,041,868 B2 | 5/2006 | Greene et al. |
| RE39,172 E | 7/2006 | Bayon et al. |

(Continued)

FOREIGN PATENT DOCUMENTS

| | | |
|---|---|---|
| EP | 486294 A2 * | 5/1992 |
| EP | 0 625 891 B1 | 1/1997 |

(Continued)

OTHER PUBLICATIONS

Freier, T., et al. 2005 Biomaterials 26: 5872-5878.*
Collins et al., Use of collagen film as a dural substitute: Preliminary animal studies, Journal of Biomedical Materials Research, vol. 25, pp. 267-276 (1991).
European Search Report corresponding to European Application No. EP 12 19 4841.8, completed on Jun. 12, 2013 and mailed on Jun. 19, 2013; 5 pages.
Canadian Office Action issued Oct. 29, 2015 in corresponding Canadian Patent Application No. 2,698,638, 4 pages.
Canadian Office Action issued Dec. 7, 2016 in corresponding Canadian Patent Application No. 2,698,638, 3 pages.
Hirano, S. et al., "Wet Spun Chitosan-Fibers, Their Chemical N-modifications, and Blood Compatibility," Biomaterials, May 2000, pp. 997-1003, vol. 21, Issue 10.

*Primary Examiner* — Marsha Tsay

(57) ABSTRACT

A bioresorbable and biocompatible compound for surgical use is composed of functionalized collagen cross-linked with a glycosaminoglycan.

16 Claims, 10 Drawing Sheets

(56) References Cited

U.S. PATENT DOCUMENTS

| | | |
|---|---|---|
| 7,098,315 B2 | 8/2006 | Schaufler |
| 7,175,852 B2 | 2/2007 | Simmoteit et al. |
| 7,192,604 B2 | 3/2007 | Brown et al. |
| 7,214,765 B2 | 5/2007 | Ringeisen et al. |
| 7,226,611 B2 | 6/2007 | Yura et al. |
| 2001/0008930 A1 | 7/2001 | Tayot et al. |
| 2003/0013989 A1 | 1/2003 | Obermiller et al. |
| 2003/0114937 A1 | 6/2003 | Leatherbury et al. |
| 2003/0133967 A1 | 7/2003 | Ruszczak et al. |
| 2003/0232746 A1 | 12/2003 | Lamberti et al. |
| 2004/0059356 A1 | 3/2004 | Gingras |
| 2004/0101546 A1 | 5/2004 | Gorman et al. |
| 2004/0215231 A1 | 10/2004 | Fortune et al. |
| 2005/0002893 A1 | 1/2005 | Goldmann |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2006/0094318 A1 | 5/2006 | Matsuda et al. |
| 2006/0135921 A1 | 6/2006 | Wiercinski et al. |
| 2006/0147501 A1 | 7/2006 | Hillas et al. |
| 2006/0167561 A1 | 7/2006 | Odar et al. |
| 2006/0216320 A1 | 9/2006 | Kitazono et al. |
| 2006/0252981 A1 | 11/2006 | Matsuda et al. |
| 2007/0031474 A1 | 2/2007 | Tayot |
| 2007/0161109 A1 | 7/2007 | Archibald et al. |
| 2007/0280990 A1 | 12/2007 | Stopek |

FOREIGN PATENT DOCUMENTS

| | | |
|---|---|---|
| EP | 0 693 523 B1 | 11/2002 |
| EP | 1 384 774 A1 | 1/2004 |
| EP | 1 315 468 B1 | 6/2005 |
| EP | 1 561 480 A2 | 8/2005 |
| EP | 1 017 415 B1 | 10/2005 |
| EP | 1 484 070 B1 | 1/2006 |
| EP | 1 782 848 A2 | 5/2007 |
| FR | 2 715 405 A1 | 7/1995 |
| WO | WO 98/31345 A1 | 7/1998 |
| WO | WO 03/002168 A1 | 1/2003 |
| WO | WO 2004/078120 | 9/2004 |
| WO | WO 2005/112820 A2 | 12/2005 |
| WO | WO 2007/048099 A2 | 4/2007 |

* cited by examiner

BIORESORBABLE AND BIOCOMPATIBLE COMPOUNDS FOR SURGICAL USE

CROSS-REFERENCE

This application is a continuation of and claims the benefit of U.S. patent application Ser. No. 11/899,694 filed on Sep. 7, 2007, the entire content of which is hereby incorporated by reference.

TECHNICAL FIELD

The present disclosure relates to biocompatible and bioresorbable compounds containing a functionalized collagen covalently bonded directly to a glycosaminoglycan without the use of a chemical cross-linking agent. The present compounds and compositions containing them are useful for a variety of medical applications, including surgical implants.

DESCRIPTION OF THE RELATED ART

Collagen and glycosaminoglycans have been combined for the preparation of biomaterials and surgical implants. Non-crosslinked collagen and chitosan mixtures have weak mechanical properties rendering their manipulation difficult and the in-vivo biodegradation of the collagen is often insufficient.

Cross linking of collagen and glycosaminoglycans, e.g. chitosan, using a cross linker agent such as glutaraldehyde is inconvenient in certain applications. For example, the use of glutaraldehyde in aqueous media leads to the formation of very high molecular glutaraldehyde polymers which are difficult to eliminate by simple washing techniques. Upon implantation, such glutaraldehyde polymers may hydrolyse and cause a release of glutaraldehyde or remain in-vivo and be liberated after the disappearance of the collagen/chitosan components.

It would be advantageous to provide biocomposites or implants made of functionalized collagen and glycosaminoglycans. The formulation advantageously provides a tailor-made, self cross-linked glycoprotein network and may be based on highly purified and fully characterized extracellular matrix compounds which mimic the native extracellular matrix and provide an optimal support for cell differentiation and growth and for tissue regeneration. The relative amounts of oxidized collagen and glycosaminoglycans may be varied to optimize the biological, mechanical and biodegradation properties of the appropriate tissue to be repaired and/or regenerated. When compared to implants based only on collagen, the formulations described herein can also favor the repair and/or the regeneration of tissues by the release of glycosaminoglycan oligomers, showing interesting biological properties (eg. angiogenic, antibacterial properties), in a time controlled fashion. The formulations can be also advantageously obtained under different physical forms by itself (eg. gel, film, sponge, yarn, knitted textile, woven textile, non-knitted non-woven mesh) or can be easily combined with other components in an open fashion.

SUMMARY

Accordingly, the present disclosure relates to compounds containing a functionalized collagen covalently bonded directly to a glycosaminoglycan without the use of a chemical cross-linking agent. In particular embodiments, the collagen is functionalized by oxidative cleavage which converts pendant portions of the collagen molecule into aldehydes which are reactive with the amine groups of the glycosaminoglycan. Methods for preparing the compounds are also described.

The present compounds may be used to form a variety of surgical implants such as gels, films, sponges, fibers, woven textiles, knitted textiles, non-woven, non-knitted textiles, and the like. In embodiments, the compounds may be combined with a substrate to form a coated implant or to add additional layers to the implant.

BRIEF DESCRIPTION OF THE DRAWINGS

The embodiments of the present disclosure will be described more clearly by means of the description which follows and the attached drawings in which.

DETAILED DESCRIPTION

Figure 1:
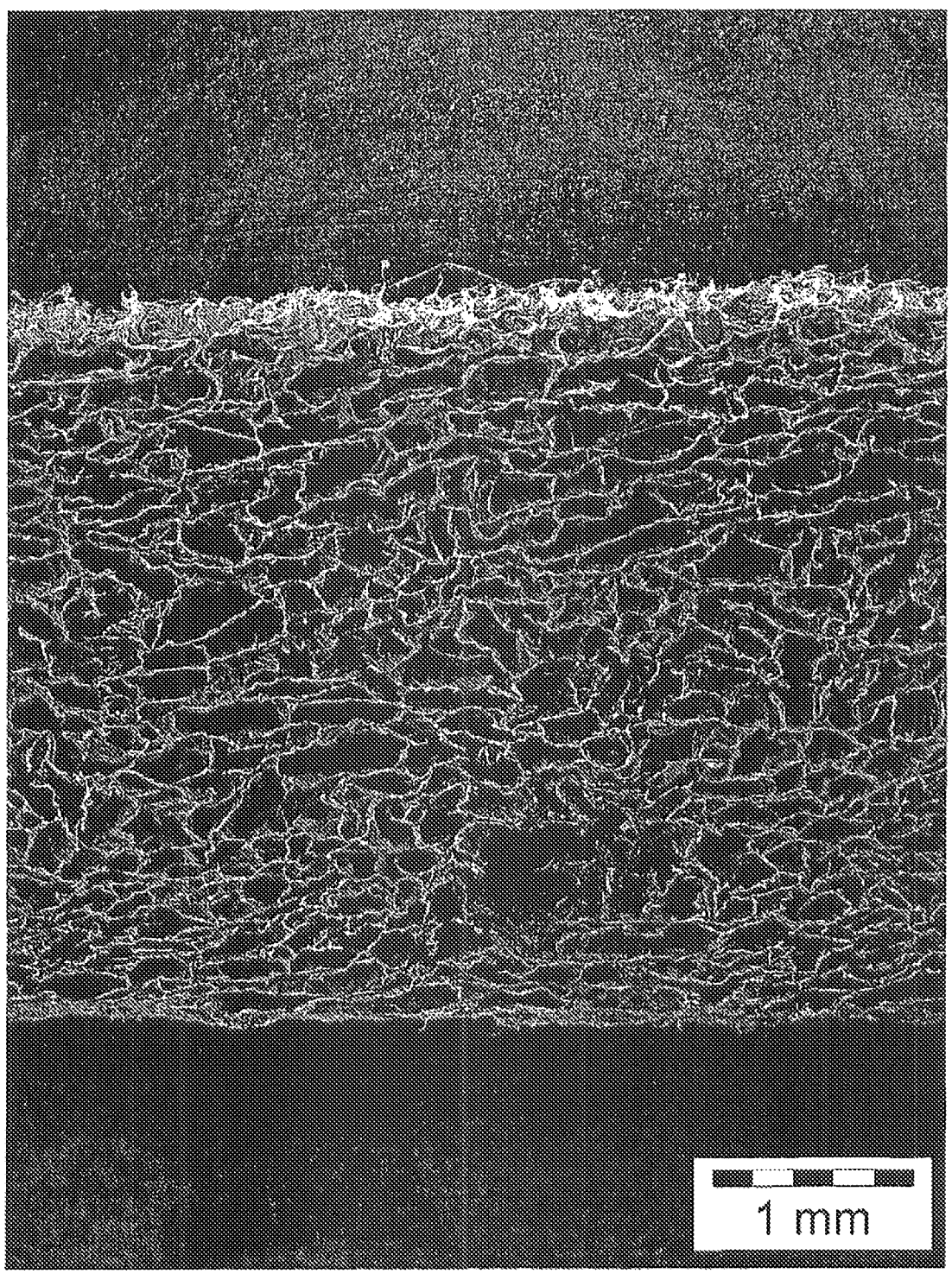
FIG. 1 represents a scanning electron microscopy image (Hitachi S800 scanning electron microscope with image acquisition and analysis system) of a freeze dried sponge according to the present disclosure, made from a 50/50 oxidized collagen (CXN)/chitosan mixture, from a side view.

Compounds containing a functionalized collagen covalently bonded directly to a glycosaminoglycan without the use of a chemical cross-linker agent are provided in accordance with the present disclosure. In embodiments, the compounds may be obtained by combining a reactive solution of collagen or gelatine, modified by a chemical reaction (e.g. oxidative cleavage) to functionalize a pendant portion of the collagen with moieties which are capable of forming a covalent bond with the reactive moieties of the glycosaminoglycan. The compounds, processes for preparing the compounds and design of surgical implants using the compounds are described in greater detail below. The methods for producing the product of the present disclosure make use of steps that are recognized as effective for inactivating viral particles and prions. Advantageously, the collagen and glycosaminoglycan may be highly purified and totally free of pendant residues providing a real advantage comparatively to the extracellular matrix made from biological tissues such as small intestine, sub mucosa or dermis. This gives the product a very high safety level while eliminating the inflammatory response.

Collagen

Collagen is a naturally occurring protein featuring good biocompatibility. It is the major structural component of vertebrates, forming extracellular fibers or networks in practically every tissue of the body, including skin, bone, cartilage, and blood vessels. In medical devices, collagen provides a more physiological, isotropic environment that has been shown to promote the growth and function of different cell types, facilitating the rapid overgrowth of host tissue after implantation.

For the purpose of the present application, the term "collagen" is intended to mean any known collagen of porcine, bovine or human origin, for example natural or recombinant collagen, esterified collagen, for example methylated, ethylated or alternatively succinylated collagen, glycosylated collagen (eg. collagen glycosylated with saccharides/polysaccharides comprising free amino groups, collagen glycosylated with saccharides/polysaccharides comprising vicinal diols, collagen glycosylated with saccharides/polysaccharides comprising —$CH_x(NH_2)$—$CH_y$(OH)— chemical bonds), or one of its derivatives.

The term "gelatine" here includes commercial gelatine made of collagen which has been denatured by heating and in which the chains are at least partially hydrolyzed (molecular weight lower than 100 kDa).

The collagen used can be of human or animal origin. Some non-limiting examples include, type I porcine or bovine collagen, type I or type III human collagen or mixtures in any proportions of these types. In embodiments, the collagen or gelatine used is a porcine collagen.

The collagen can be modified by using any method known to those skilled in the art to provide pendant portions of the collagen with moieties which are capable of covalently bonding with the reactive chemical groups of a glycosaminoglycan. Examples of such pendant moieties include aldehydes, sulfones, vinylsulfones, isocyanates, and acid anhydrides. In addition, electrophilic groups such as —$CO_2N(COCH_2)_2$, —$CO_2N(COCH_2)_2$, —$CO_2H$, —CHO, —$CHOCH_2$, —N=C=O, —$SO_2CH$=$CH_2$, —$N(COCH)_2$, —S—S—($C_5H_4N$) may also be added to pendant chains of the collagen to allow covalent bonding to occur with the glycosaminoglycans.

In embodiments, the collagen may be modified through the addition of an oxidizing agent. Contacting collagen with an oxidizing agent creates oxidative cleavage along portions of the collagen thereby creating pendant aldehyde groups capable of reacting with the glycosaminoglycans. The oxidizing agent may be, for example, iodine, peroxide, periodic acid, hydrogen peroxide, a periodate, a compound containing periodate, sodium periodate, a diisocyanate compound, a halogen, a compound containing halogen, n-bromosuccinimide, a permanganate, a compound containing permanganate, ozone, a compound containing ozone, chromic acid, sulfuryl chloride, a sulfoxide, a selenoxide, an oxidizing enzyme (oxidase) and combinations thereof. In embodiments, the oxidizing agent is periodic acid.

An example of the oxidative technique is described by Tardy et al. in U.S. Pat. No. 4,931,546, the entire content of which is herein incorporated by reference. Briefly, this technique involves mixing the collagen in acid solution with an oxidizing agent, i.e., a solution of periodic acid or one of its salts, at a concentration of between 1 and $10^{-5}$ M, in embodiments between 5 $10^{-3}$ and $10^{-1}$ M, at a temperature of between 10 and 25° C. for 10 minutes to 72 hours. This process breaks down hydroxylysine and the sugars of the collagen, thus creating reactive sites without causing cross-linking. The oxidative cleavage of collagen allows moderate cross-linking later in the collagenic material.

Another technique for oxidized collagen is by oxidation of a 3% collagen solution by periodic acid, at a final concentration of 8 mM, during 3 hours, as described by Bayon, et al. in U.S. Pat. No. 6,596,304, the entire content of which is herein incorporated by reference. Aldehyde groups are formed by oxidative cleavage on the lateral chains of the hydroxyl-lysine residues giving the oxidized collagen capabilities to form covalent bonds with amines. The oxidized collagen can be fully degraded in vivo, after a few weeks, and while not wishing to be bound by any theory, it is believed that the oxidized collagen will degrade before the glycosaminoglycan.

Glycosaminoglycans

The term "glycosaminoglycan" is intended to encompass complex polysaccharides having repeating units of either the same saccharide subunit or two different saccharide subunits. Some non-limiting examples of glycosaminoglycans include dermatan surfate, hyaluronic acid, the chondroitin sulfates, chitin, heparin, keratan surfate, keratosulfate, and derivatives thereof. Some non-limiting examples of derivatives may include partially and fully deacylated versions of these compounds such as chitosan and deacylated hyaluronic acid. The glycosaminoglycans may be extracted from a natural source, e.g. animal tissues such as squid pens and shrimp shells or vegetable sources such as mushrooms (eg "champigon de paris"), or they may be synthetically produced or synthesized by modified microorganisms such as bacteria.

In embodiments, the functionalized collagen may be combined with a glycosaminoglycan such as chitosan to crosslink and form covalent bonds. The glycosaminoglycan displays a degree of acetylation (DA) of about 0% to about 60%. In embodiments, the glycosaminoglycan displays a degree of acetylation (DA) of about 0.5% to about 50%. Samples of different degrees of acetylation can be obtained either by a heterogeneous deacetylation process or by a homogenous reacetylating process from a sample of a glycosaminoglycan that is fully deacetylated.

In embodiments, the glycosaminoglycan has a molecular weight ranging from about 100 to about 1,000,000 g/mol. In some embodiments, the glycosaminoglycan has a molecular weight ranging from about 164 (chitosan monomer) to about 1,000,000 g/mol. In addition, the glycosaminoglycan also displays a low polydispersity index between about 1.2 to about 1.8. In particularly useful embodiments, the glycosaminoglycan is chitosan. Nevertheless, the glycosaminoglycan may be a mixture of chitosans with different degrees of acetylation or a mixture of chitosans and other glycosaminoglycans, e.g. hyaluronic acid, with different degrees of acetylation and in which all glycosaminoglycan have the capability, i.e. have free amino groups, to be cross-linked to the oxidized collagen.

Combining the Functionalized Collagen and the Glycosaminoglycans

Compounds in accordance with the present disclosure are made by reacting a functionalized collagen with a glycosaminoglycan under conditions which cause the two components to form covalent bonds without the use of a chemical crosslinking agent. The two components may take the form of any solution, suspension, emulsion, semi-solid, or solid material capable of allowing the two-components to interact and crosslink.

In embodiments, each component is solubilized in an acceptable solvent such as deionized water to from two separate solutions. The two solutions may be combined to allow the two components to mix and form the compounds described herein. In particular embodiments, the glycosaminoglycan is solubilized in deionized water with a stoechiometric amount of hydrochloric acid with a polymer concentration ranging from about 0.5% to about 10% (w/w). It is envisioned that the pH of the glycosaminoglycan solution can be adjusted if necessary between about 2 and about 7.5 depending on the degree of acetylation. The functionalized collagen is also solubilized in an acceptable solvent such as deionized water to a concentration ranging from about 0.5% to about 10% (w/w). It is also envisioned that the pH of the functionalized collagen solution may be adjusted between about 2 and about 7.5. The two components in solution are mixed to a final concentration of polymer comprising 0.5% and 20% (w/w). In embodiments, different proportions between the functionalized collagen and the glycosaminoglycan may be used. In particular embodiments, the glycosaminoglycan may be composed of a mixture of chitosans with different degrees of acetylation (DA). The chitosan having a degradation time in function with its degree of acetylation (K. Kurita et al, Carbohydrate polymers. Vol 42 pp. 19-21,200; K. Tomihata et al, Biomaterials. Vol 18 no 7 pp. 567-575,1997), the combination of slow and fast biodegradable chitosan is an important issue for the awaiting properties of the implant, i.e., progressive cell colonization of the sponge. In fact, the degradation of the slow biodegradable oxidized collagen and chitosan with high DA, i.e. 35≤DA≤50, in vitro in the presence of viable cells and in vivo, helps to increase the interconnected porosity which is a key parameter for the regeneration of healthy native like tissue in the full thickness of the implant and the extent of tissue integration. In embodiments, molecules released from the controlled degradation of the biocomposite, for example oxidized collagen/chitosan, may advantageously confer to the implant highly interesting biological activities e.g. antimicrobial, anticancer, antioxidant, and immunostimulant effects, especially in the case of chitosan (S-K. Kim et al, Carbohydrate Polymers, Vol. 62, Issue 4, pp. 357-368,2005) and may bring, in complement of the biocompatibility and biodegradability, bioactive properties to the medical devices. The biological properties of released chitosan oligopolymers enhance the tissue regeneration and extend the use of the implant, e.g. to surgical sites with a high risk of contamination.

In embodiments, a combination of two solutions comprising an acidic solution of oxidized collagen and an acidic solution of chitosan with one or a mix of several degree of acetylation. The collagen is oxidized by the addition of periodic acid as the oxidizing agent and the chitosan solution is made acidic by the addition of hydrochloric acid. The mixture can be neutralized either with an alkaline vapour/solution or buffer solution with a pH greater than 7, leading to a cross-linked scaffold compatible for cell adhesion and proliferation. This combination is particularly advantageous compared to a combination of oxidized collagen and glutaraldehyde cross-linked collagen, because the latter makes a suspension which is difficult to incorporate in a homogeneous fashion to an implantable surgical device such as a three-dimensional mesh.

Viscosity of the Mixture of Native Collagen/Glycosaminoglycan Versus Functionalized Collagen/Glycosaminoglycan The reaction between the functionalized collagen and glycosaminoglycan is characterized by a rapid increase of the viscosity of the reaction mixture when the two components are mixed. Viscosity measurements were performed on a viscosimeter Lamy type TVe-05. The solutions of oxidized collagen and chitosan were equilibrated at the temperature of 25° C. for 1 hour and then mixed. A sample of 5 ml was poured into the chamber of the viscosimeter and the evolution of viscosity against time was studied. The viscosity of the solution composed of oxidized collagen and chitosan and a solution composed of native collagen and chitosan were compared to highlight the type of interactions between the oxidized collagen and the chitosan.

The tests were performed at 25° C. with biopolymers having characteristics described below:

Chitosan DA=2.5% and Mw=500,000 g/mol

Oxidized collagen (CXN) prepared from native collagen by oxidative cleavage.

Native collagen (CPP) without telopeptide and with helicoidal structure preserved. The average molecular weight is about 300,000 g/mol.

The solution prepared for the tests had a final polymer concentration of 1% (w/w), a proportion close to 50/50 respectively of collagen and chitosan. The pH measured was close to 4.7 and 4.89, respectively, for the CXN/chitosan and CPP/chitosan mixtures.

Figure 7:
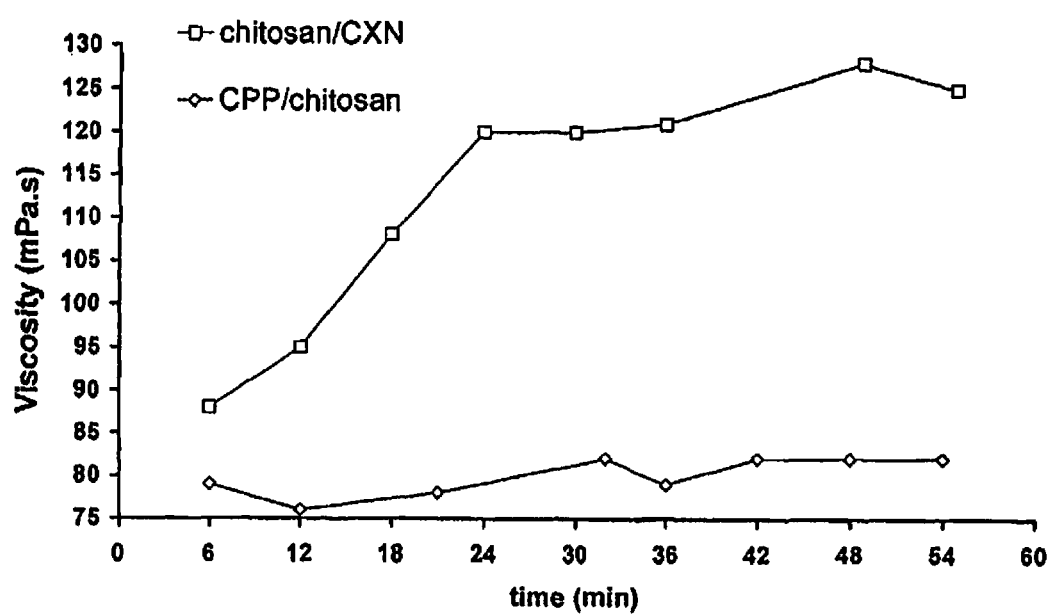
FIG. 7 represents a viscometer reading of an oxidized collagen and chitosan mixture and a native collagen and chitosan mixture in accordance with the present disclosure.

As shown in FIG. 7, there is an increase of viscosity in the case of the oxidized collagen/chitosan mixture wherein the area of stability was reached for 30 minutes at a pH of 4.7. On the other hand, only a slight increase of viscosity is observed in the case of the native collagen/chitosan solution. Therefore, the difference of the viscosity evolution against time can be attributed, partly, to the formation of a chemical crosslink between oxidized collagen and chitosan. In fact, the low viscosity increase in the case of chitosan/native collagen mixture is due to the ionic complex because the two components exhibit a high charge of density.

Surgical Implant Design using the Oxidized Collagen and Chitosan Mixture

The cross-linked mixture of functionalized collagen and a glycosaminoglycan can be used to form a variety of surgical implants such as sponges, films, hydrogels, non-woven non-knitted meshes, three-dimensional structures such as tubular and spherical structures, microbeads, threads, rods, filaments, yarns, meshes, slings, sutures and other composite materials such as pledgets, buttresses, adhesion barriers and the like. The mixture can also be combined with or used to coat surgical implants, such as two-dimensional meshes, three-dimensional meshes, vascular prostheses, patches, slings and the like.

The surgical implants which may be combined or coated with compositions which include the compounds of the present disclosure may be made from bioabsorbable or non-bioabsorbable materials. Some non-limiting examples of suitable non-absorbable materials which may be utilized included polyolefins, such as polyethylene, polypropylene, copolymers of polyethylene and polypropylene, and blends of polyethylene and polypropylene. Other non-absorbable materials which may be utilized include polyesters such as polyethylene terephthalate (PET), polyamides, aramides, expanded polytetrafluoroethylene, polyurethane, polyvinylidene, difluoride (PVDF), polybutester, copper alloy, silver alloy, platinum, medical grade stainless steels such as 316 L medical grade stainless steel, combinations thereof, and the like. Examples of commercially available polypropylene-based textile supports which may be utilized include those sold under the brand name PARIETENE® from Sofradim.

Suitable absorbable materials include, but are not limited to, trimethylene, carbonate, caprolactone, dioxanone, glycolic acid, lactic acid, glycolide, lactide, homopolymers thereof, copolymers thereof, and combinations thereof. Specific absorbable materials which may be suitable include, for example, chitosan, cellulose, oxidized cellulose, combinations thereof, and the like.

In embodiments, a solution of the present compounds may be freeze-dried to form a porous sponge material capable of allowing tissue in growth and induce a progressive cell colonization of the sponge by mixing several glycosaminoglycans with different degrees of acetylation and with different degradation properties. In embodiments, the solutions described herein may include additional polymeric materials which allow the solution to form a non-porous film useful in preparing adhesion barriers. In particular, the compounds may be combined with polyethylene glycol, and glycerol to form a nonporous film. In still other embodiments, the sponges or films or hydrogel materials as described herein may be used to add a coating layer on an existing surgical implant or to form a multilayer surgical implant. Such combination implants may be useful in forming surgical implants which prevent adhesions and the in-growth of tissue one side of the implant and encourage the in-growth of tissue and formation of adhesions on the other side of the implant. Some non-limiting examples include multilayer pledgets, buttresses, surgical meshes, slings and adhesion barriers.

In embodiments, a solution of the present compounds may be used to form yarn by a wet spinning process as described in the patent EP0328050A2 by Bisento de rutsuka et al. The biological composite yarns are fully biocompatible and biodegradable with a wide range of degradation times due to the mix of several glycosaminoglycans with different degrees of acetylation. The composite yarns may be used to knit textiles with different patterns in 2 or 3 dimensions and these yarns may be used alone or combined with other biocompatible yarns such as yarns made from polylactic acid (PLA). The textiles may be employed as implants or as a part of an implant to improve the mechanical properties of the implant. Moreover with the collagen/glycosaminoglycan composition, the textile may have high biocompatibility and good mechanical properties in a wide range of degradation times, ranging from about 2 weeks to several months. Advantageously, the molecules released from the degradation of the biocomposite, for example oxidized collagen/chitosan, give biological activities of particular interest, i.e., antimicrobial, anticancer, antioxidant, and immunostimulant effects, especially in the case of chitosan.

Optional Bioactive Agents

In embodiments, at least one bioactive agent may be included in compositions containing the present compounds and thereby incorporated into a medical device. In these embodiments, the implant can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the medial device in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to poly(vinyl pyrrolidone), carboxymethyl cellulose, hyaluronic acid, polyethylene oxide, poly vinyl alcohols and combinations thereof.

Suitable antimicrobial agents which may be included as a bioactive agent in the bioactive coating of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B and antimicrobial polysaccharides such as fucans and derivatives may be included as a bioactive agent in the bioactive coating of the present disclosure.

Other bioactive agents which may be included as a bioactive agent in the coating composition applied in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; antimigraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; anti-histamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ((3-IFN, (a-IFN and y-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Bioactive agents can also be additives, such as fucans, either native or chemically modified glucosaminoglycans, oxidized starch, emulsifiers, surfactants, humectants, buffering agents, pH modulators, chelating agents, viscosity agents and any other products which may enhance tissue repair, limit the risk of sepsis, and modulate mechanical properties of the compounds.

EXAMPLES

The following non-limiting examples show the preparation, formulation and uses possible of the present compounds and the tensile and swelling properties of the oxidized collagen and chitosan mixture compared to a native collagen and chitosan mixture.

Example 1

Freeze Dried Sponge for the Preparation of Materials Supporting Cell Growth

A collagen/chitosan mixture was prepared by mixing an acidic solution of oxidized collagen and an acidic solution of chitosan in different proportions with a final polymer concentration of 1% (w/w).

Oxidized Collagen

Oxidized collagen was obtained by the oxidation of a 3% collagen solution by periodic acid, at a final concentration of 8 mM, at room temperature, during 3 hours, as described by Bayon, et al. in Example 4 of U.S. Pat. No. 6,596,304. At this step the pH of the oxidized collagen solution was about 3.2.

Native Collagen

Solutions of native collagen were obtained by solubilizing collagen powder at a 1% final concentration, in sterile water. The pH measured close to 3.

Chitosan

The chitosan was solubilized in deionized water with a stoechiometric amount of hydrochloric acid with a polymer concentration of 1% (w/w). The pH of the chitosan solution was about 5, but the pH could have been adjusted to 3 to have better control of the crosslink kinetic between the oxidized collagen and chitosan.

Before freeze drying, if the application required it, the collagen/chitosan mixture could have been poured into a 3D mesh so as to fully cover the mesh and obtain a freeze dried sponge/mesh composite. The presence of the 3D mesh facilitates fastening the implant to tissue (e.g., via suturing). Moreover, the homogeneity of the oxidized collagen/chitosan solution allows a better penetration of the solution within a 3-dimensional structure of the textile when compared to collagen that has been oxidized with a cross-linking agent.

Freeze Dried Composite

Several mixtures of various blends of oxidized collagen and chitosan as well as native collagen and chitosan (approximately 121 g) were poured within a 12 cm by 17 cm plastic box and freeze-dried for 24 hours. The samples were then neutralized in a 1M sodium hydroxide bath for 1 hour and thoroughly washed in deionized water until the pH reached 7. The freeze-dried sponges were then calendered to obtain a material with a final thickness of 0.13 mm.

FIG. 1 represents a scanning electron microscopy image of one face of such a sponge.

Additives, such as fucans, native or chemically modified glucosaminoglycans, which may induce self chemical cross-link between collagen and glucosaminoglycans (hyaluronic acid, sulphate chondroitin, etc), oxidized starch, and any other product which may enhance tissue repair, limit the risk of sepsis, and modulate the mechanical properties of the composite (swelling rate in water, tensile strength, etc) could have been be added to the blend of oxidized collagen and chitosan.

Tensile Tests on Freeze-Dried Calendered Sponges Composed of Native Collagen/Chitosan and Oxidized Collagen/Chitosan Tensile and suture tests were performed per Hounsfield H5KS at room temperature on calendered freeze-dried sponges. Several blends of the native collagen and chitosan mixture and the oxidized collagen and chitosan mixture were prepared as described below in Table 1:

TABLE 1

Composition of collagen (oxidized or native) and chitosan of different freeze-dried calendered sponges.

| Batch | % Oxidized collagen (w/w) | % Native collagen (w/w) | % Chitosan (w/w) | % Polymer (w/w) |
|---|---|---|---|---|
| RHF00004 | / | 50 | 50 | 1 |
| RHF00006 | 80 | / | 20 | 1 |
| RHF00007 | 50 | / | 50 | 1 |
| RHF00008 | 20 | / | 80 | 1 |

Several amounts of various blends (121 g) were poured within 12 cm by 7 cm plastic boxes and freeze-dried for 24 hours. The samples were cut to desired dimensions as described below in Table 2, neutralized, and washed in deionized water. The freeze-dried sponges were calendered to obtain a material with a final thickness of 0.13 mm. The mechanical tests were performed on hydrated samples at a speed of 50 mm/min.

TABLE 2

Dimensions of the samples for mechanical tests

| | Dimensions |
|---|---|
| Tensile test | 2.5 × 4 cm |
| Suture test | 4 × 4 cm |

The results, summarized in Table 3, exhibit an increase in the breaking strength of the samples with the amount of chitosan present. Moreover, batch FHF00004 (native collagen and chitosan with a 50/50 blend) has lower mechanical properties than RHF00007 (oxidized collagen and chitosan with a 50/50 blend). The greater mechanical values of the RHF00007 batch confirm the chemical network in the case of a blend composed of chitosan and oxidized collagen.

TABLE 3

Breaking strength and deformation of the different batches of calendered, freeze-dried sponges determined by tensile and suture tests.

| | Tensile Tests | | Suture Tests |
|---|---|---|---|
| Batch | Breaking Strength (N) | Deformation (%) | Breaking Strength (N) |
| RHF00004 | 4.78 | 57.1 | 0.68 |
| RHF00006 | 0.51 | 32 | / |
| RHF00007 | 8.34 | 39.4 | 0.67 |
| RHF00008 | 7.75 | 61.7 | 1.46 |

Swelling Properties of the Freeze-Dried Sponges

The thickness of non-neutralized freeze-dried sponges were measured before and after the calendaring step, and then after hydration for 1 minute in a buffer (PBS I X) solution at 20° C. as shown in Table 4.

TABLE 4

Swelling properties of non-neutralized freeze-dried sponges in different states.

| | Non-calendered | Calendered | Hydrated |
|---|---|---|---|
| Oxidized collagen & Chitosan (50/50) | 3.38 mm | 0.13 mm | 0.28 mm |
| Native collagen & Chitosan (50/50) | 3.46 mm | 0.12 mm | 1.2 mm |

The values in Table 4, obtained in the case of the hydrated samples reveal increased swelling in the native collagen/chitosan composite, wherein only physical cross-linking occurred, compared to the oxidized collagen/chitosan composite, in which covalent bonds were formed.

Example 2

Preparation of Cylindrical Structures for Supporting Nervous Cells Growth

A collagen/chitosan mixture was prepared by mixing an acidic solution of oxidized collagen and acidic solution of chitosan in different proportions as described above in Example 1, with a final polymer concentration of 2% (w/w).

The mixture was poured into cylindrical moulds of different diameters ranging from 1 mm to 10 mm and freeze-dried for about 24 hours.

Thereafter, the cylinders were neutralized in a buffer solution of PBS 1× for about 2 hours and then dried in a ventilated oven at 35° C. overnight.

Example 3

Preparation of Tubular Structures for Supporting Endothelial Cells Growth

A collagen/chitosan mixture was prepared by mixing an acidic solution of oxidized collagen and acidic solution of chitosan in different proportions as described above in Example 1, with a final polymer concentration of 2% (w/w).

The mixture (about 40 g) was poured into tubular moulds of different diameters ranging from 5 mm to 15 mm and freeze-dried for 24 hours.

Thereafter, the tubes were neutralized in a buffer solution of PBS 1× for 2 hours and then dried in a ventilated oven at 35° C. overnight.

Optionally, a 20/80 mixture of the oxidized collagen and chitosan with a final polymer concentration of 0.5% (w/w) with a pH adjusted to 5 was used to coat the external surface of the tubular structure bringing different permeability properties to the tubular composite material.

Example 4

Preparation of Film for Preventing Post-Surgical Adherence

A collagen/chitosan mixture was prepared as described above in Example 1, with a final polymer concentration of 2% (w/w).

A sterile concentrated solution of PEG 4000 (polyethylene glycol having a molecular weight of 4000 daltons) and glycerol was added to the collagen/chitosan mixture, in order to achieve a PEG concentration of 1% and a glycerol concentration of 0.6%. The pH of the solution was adjusted to 6.5 by adding concentrate sodium hydroxide solution. The volume of the solution was then adjusted with sterile water to obtain final concentrations of collagen/chitosan, PEG, and glycerol, of 2%, 0.9%, and 0.54%, respectively.

The solution wais distributed in a thin layer, having a density of 0.133 g/cm$^2$, on a flat hydrophobic support of PVC or polystyrene.

The surfaces were then exposed to a sterile stream of air at 35° C., leading to complete evaporation in about 12 hours.

Additives, such as fucans, either native or chemically modified glycosaminoglycans, which may induce self-chemical crosslink between collagen and glycosaminoglycans, oxidized starch, and any other products which may enhance tissue repair, limit the risk of sepsis, and modulate the mechanical properties of the composite (such as the swelling rate in water, tensile strength, etc) may be added to the blend of oxidized collagen/chitosan.

Example 5

Oxidized Collagen/Chitosan Composite Yarns by Wet Spinning Process 100 ml of an oxidized collagen/chitosan mixture was prepared by mixing 20 g of an acidic solution of oxidized collagen (pH 3.5) and 80 g of an acidic solution of chitosan (pH 3.5) leading to a proportion of 20/80, with a final polymer concentration of 2.4% (w/w). The solution was then degassed by centrifugation for 10 min at 10 000 RPM at room temperature. The solution was spun by a spinneret with an interior diameter of 0.8 mm in a 1N sodium hydroxide bath. Then the yarn is washed with deionized water and dried ballasted by a mass of 1 g at room temperature.

Figure 2:
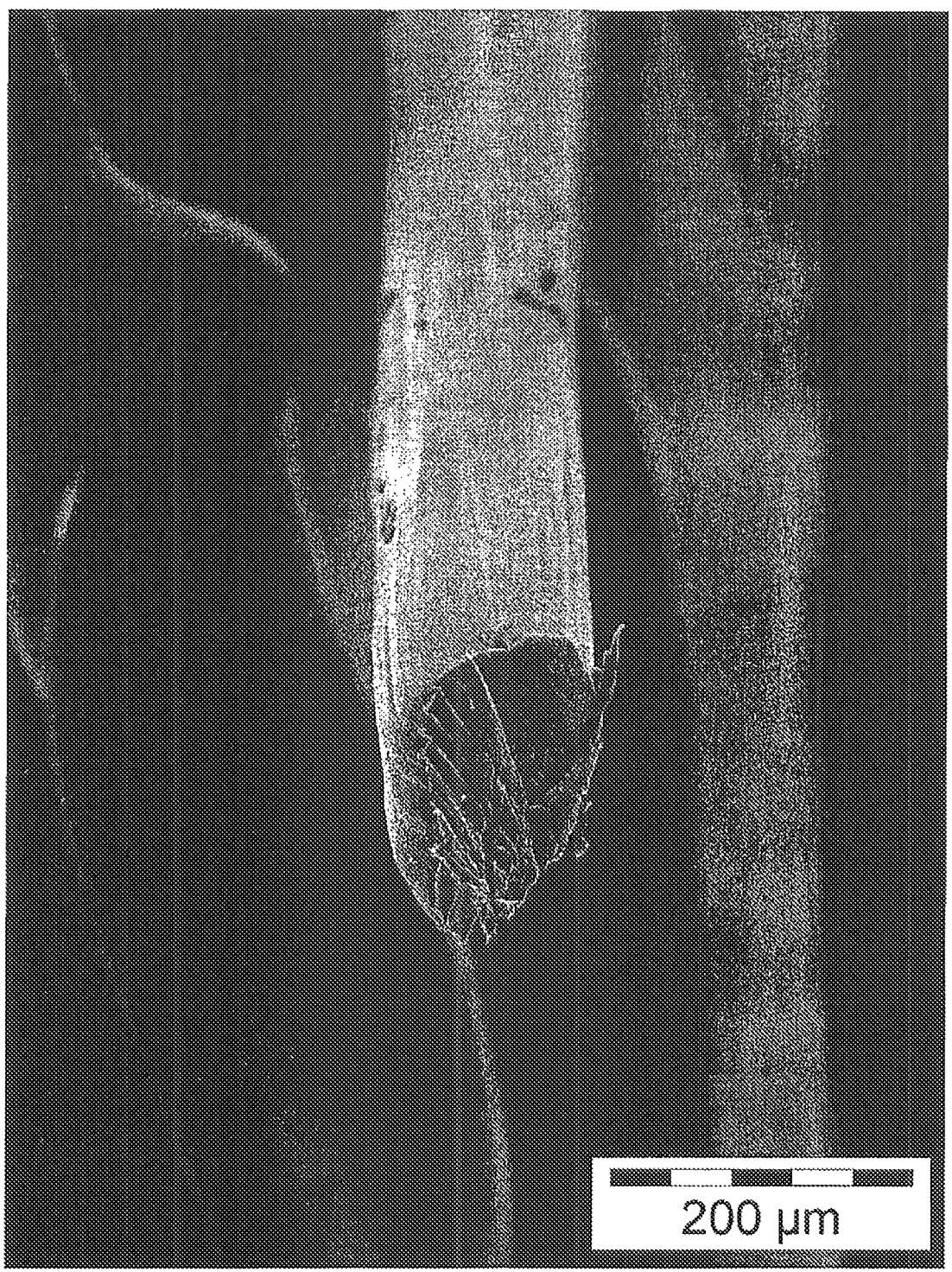
FIG. 2 represents a scanning electron microscopy image (Hitachi S800 scanning electron microscope with image acquisition and analysis system) of a yarn according to the present disclosure, made from a wet-spinning process of an CXN/chitosan mixture.

FIG. 2 represents a scanning electron microscopy image of such a yarn.

Additives, such as fucans, nanoparticles i.e. $Ag^+$ or $Cu2^+$ for they antimicrobial properties, and any other products which may enhance tissue repair, limit the risk of sepsis, and modulate the mechanical properties of the composite (such as the swelling rate in water, tensile strength, etc) may be added to the blend of oxidized collagen/chitosan.

Example 6

Oxidized Collagen/Chitosan Hydrogel 100 ml of an oxidized collagen/chitosan mixture was prepared by mixing 20 g of an acidic solution of oxidized collagen (pH 3.5) and 80 g of an acidic solution of chitosan (pH 3.5) leading to a proportion of 20/80, with a final polymer concentration of 3% (w/w). After complete homogenization, an equivalent amount of alcohol, e.g. glycerol or 1,2-propandiol, was added to the solution and the blend was gently stirred for 1 hour. The solution was degassed by centrifugation for 10 min at 10 000 RPM at room temperature. Then, 60 g of the solution was poured within 12 cm by 12 cm Petri dishes and left to evaporate in a ventilated oven at 40° C. for 24 hours. The alcohol gel was neutralized in a 4N $NH_4OH$ bath for 1 hour and then thoroughly washed in deionized water until the water pH was closed to a value of 7. The hydrogels were conserved in sterile water at 4° C.

Example 7

Mesh Coatings with Oxidized Collagen/Chitosan Mixture

Oxidized Collagen

Oxidized collagen was obtained by the oxidation of a 3% collagen solution by periodic acid, at a final concentration of 8 mM, at room temperature, during 3 hours, as described above in Example 1.

Chitosan

The chitosan was solubilized in deionized water with a stoechiometric amount of hydrochloric acid with a polymer concentration of 1% (w/w). The pH of the chitosan solution was adjusted to 3 to stop the crosslink kinetic reaction between the oxidized collagen and chitosan.

Mesh Coating

Two-dimensional or three-dimensional meshes made of PLA or PET were soaked once, twice, or three times in an oxidized collagen/chitosan mixture, then dried and neutralized with an alkaline bath so as to cover the accessible surface of the PLA or PET fibers of the mesh.

FIGS. 4 through 6B represent scanning electron microscopy images of such meshes.

Example 8

Preparation of Composite Material for Repairing Dural Defect

The present dural repair materials may include one or two non-porous layers, a porous layer, and if necessary a reinforcement member e.g. textile.

Preparation of Textile Reinforcement Member Coated with Oxidized Collagen/Chitosan Mixture Two-dimensional meshes made of PLA or PET were soaked once, twice, or three times in an oxidized collagen/chitosan mixture, then dried and neutralized with an alkaline bath so as to cover the accessible surface of the PLA or PET fibers of the mesh.

FIGS. 4A, 4B, 6A, and 6B represent scanning electron microscopy images of such two-dimensional meshes.

Three-dimensional meshes made of monofilaments and multifilament PLA threads were soaked once, twice or three times in an oxidized collagen/chitosan mixture, then dried and neutralized with an alkaline bath so as to cover the accessible surface of the PLA filaments of the mesh.

Figure 5A:
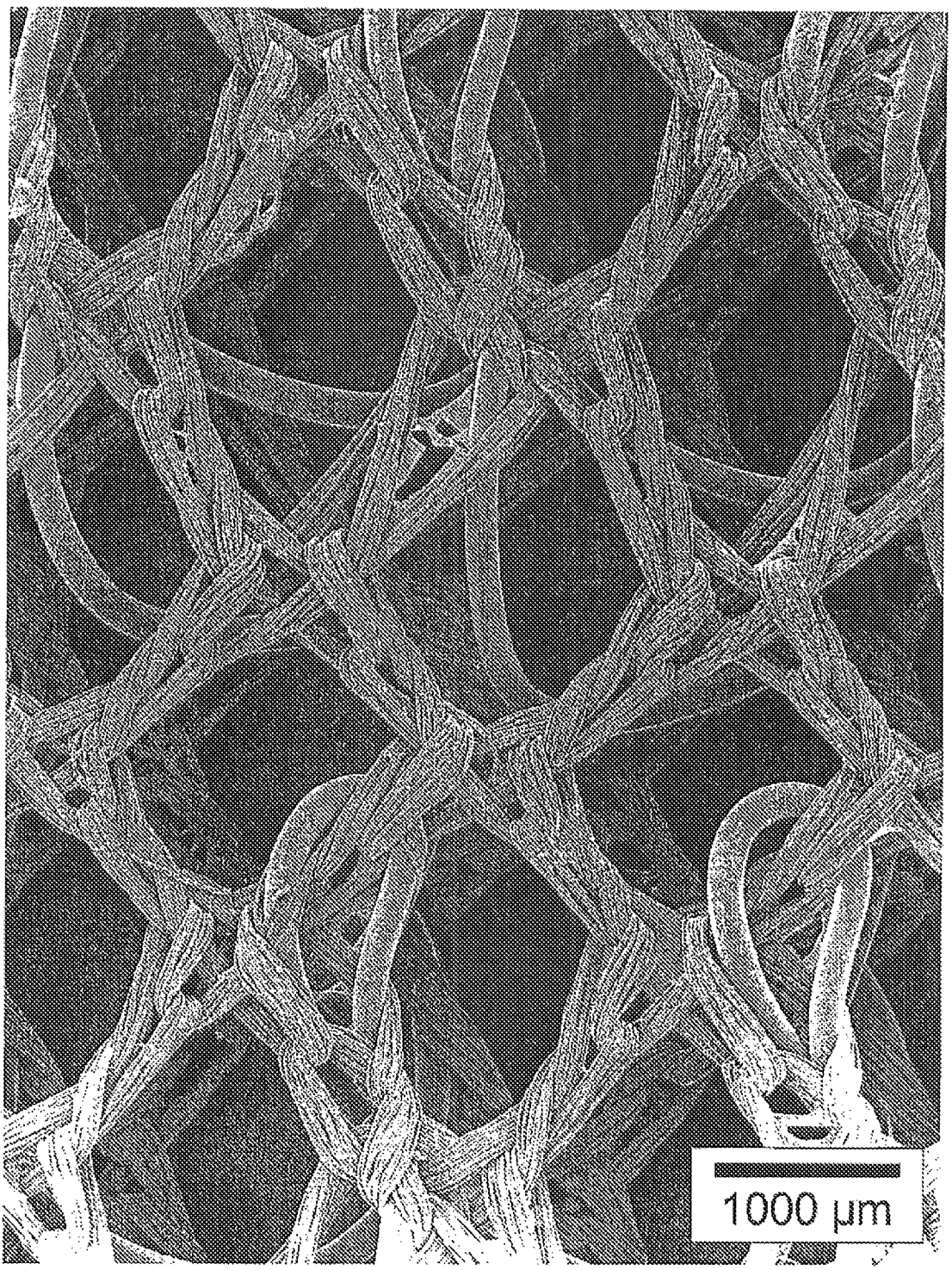
FIG. 5A represents a scanning electron microscopy images (Hitachi S800 scanning electron microscope with image acquisition and analysis system) of a three-dimensional textile according to the present disclosure, the textile being knitted with both monofilaments and multifilaments of PLA and being coated three times with a 50/50 CXN/chitosan mixture.
Figure 5B:
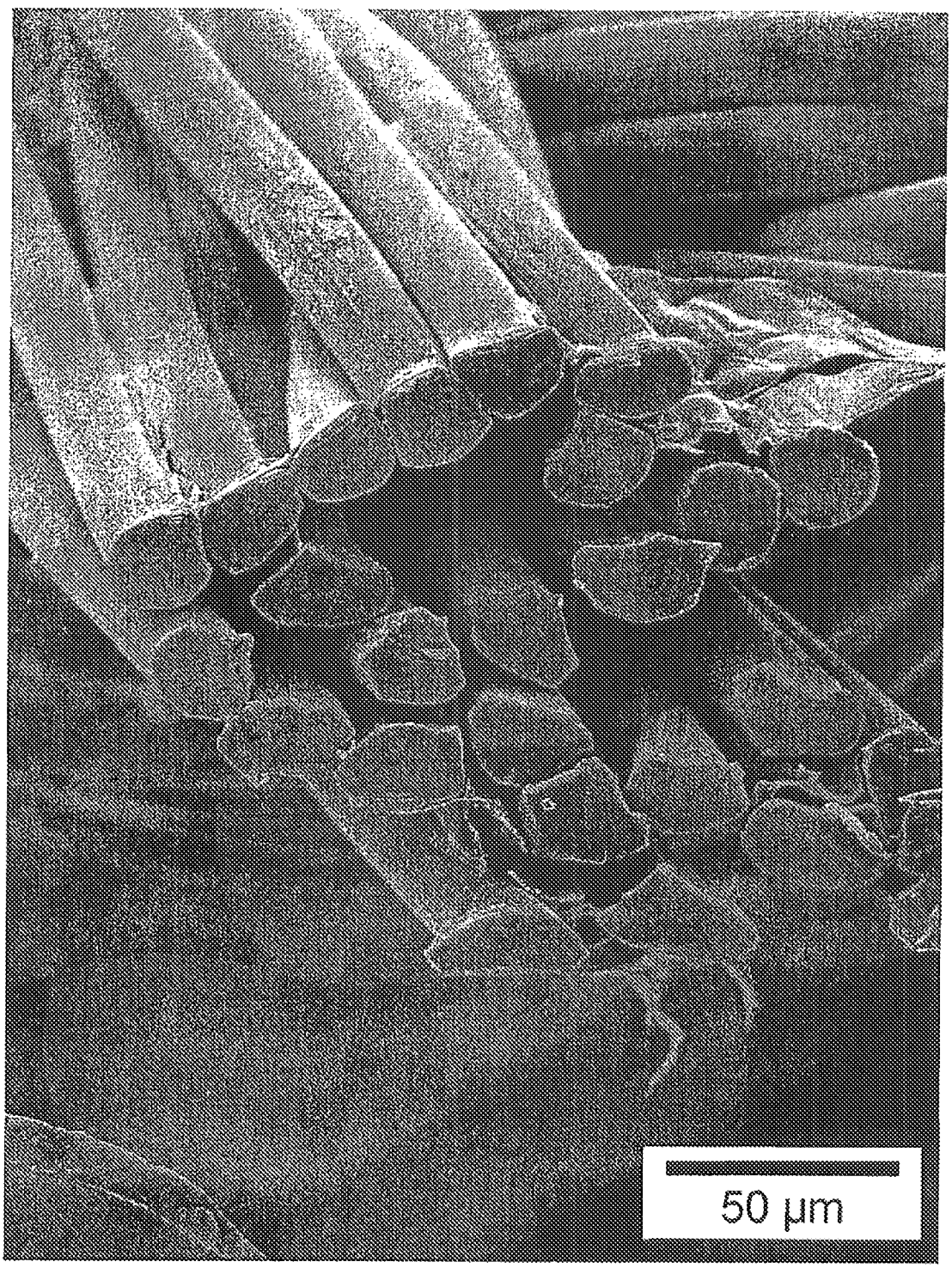
FIG. 5B represents a scanning electron microscopy images (Hitachi S800 scanning electron microscope with image acquisition and analysis system) of a three-dimensional textile according to the present disclosure, at a higher magnification than for FIG. 5A, the textile being knitted with both monofilaments and multifilaments of PLA and being coated three times with a 50/50 CXN/chitosan mixture.
Figure 6A:
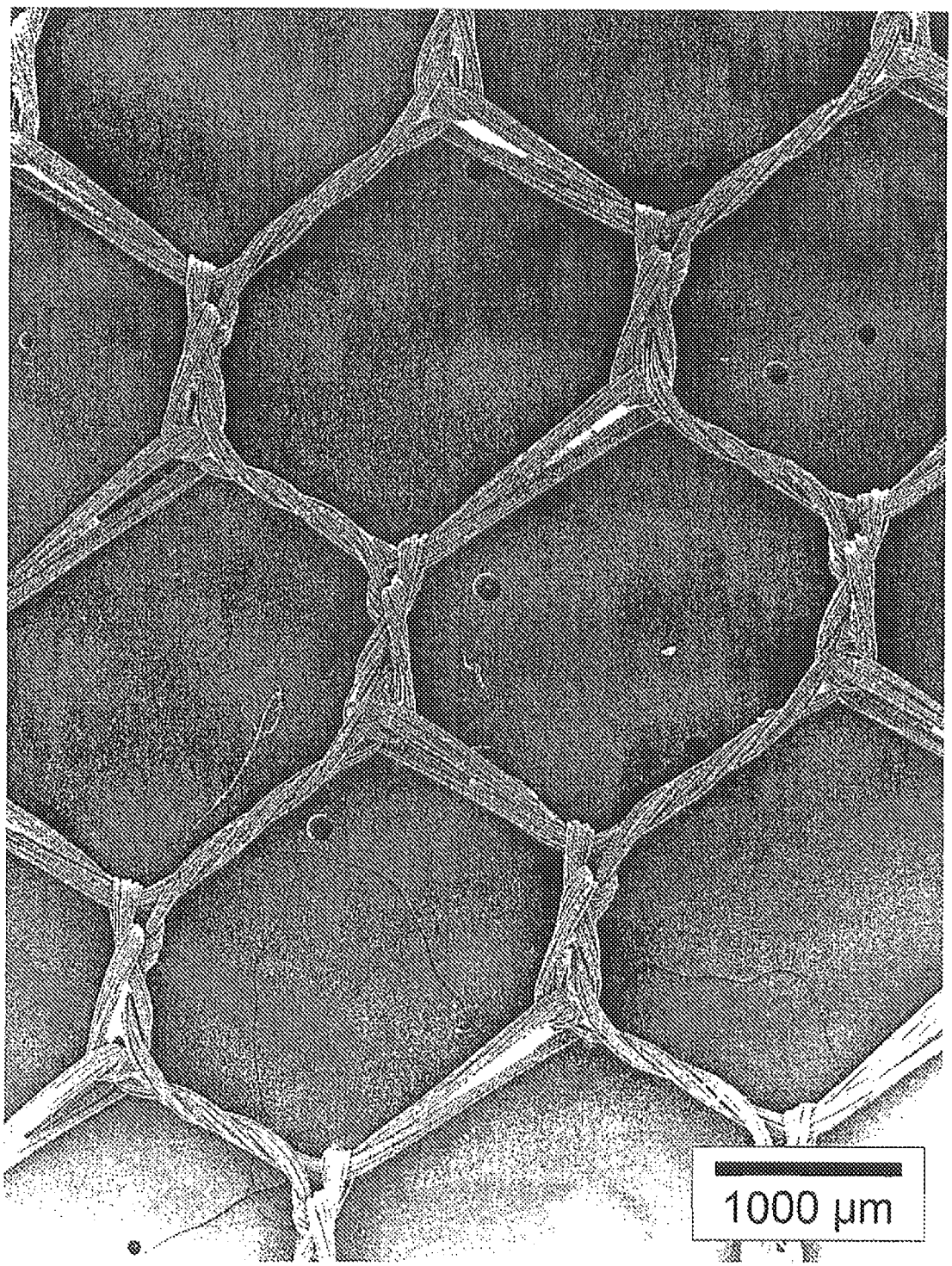
FIG. 6A represents a scanning electron microscopy images (Hitachi S800 scanning electron microscope with image acquisition and analysis system) of a two-dimensional textile according to the present disclosure, the textile being knitted with multifilaments of PET and then coated three times with a 50/50 CXN/chitosan mixture.
Figure 6B:
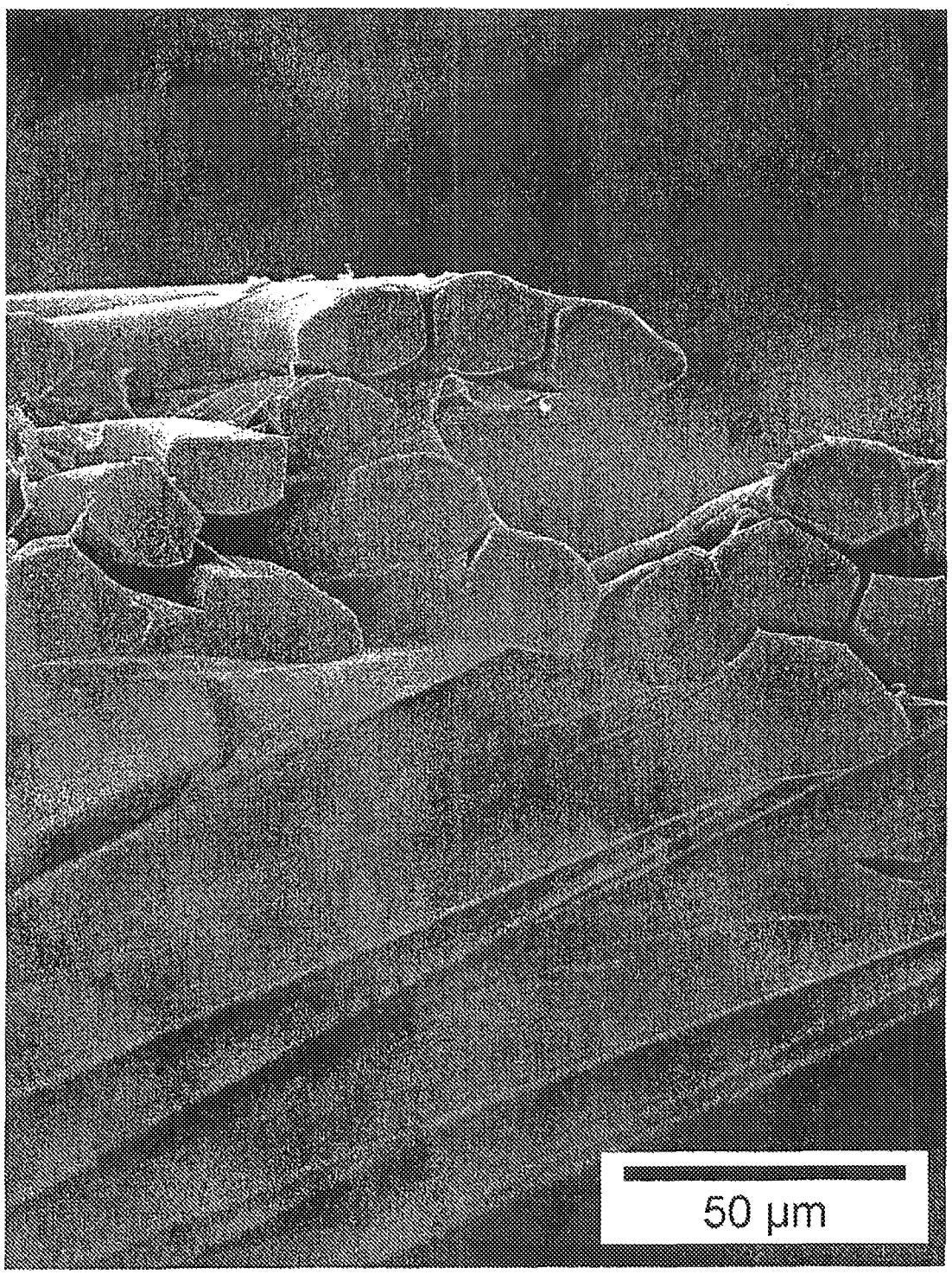
FIG. 6B represents a scanning electron microscopy images (Hitachi S800 scanning electron microscope with image acquisition and analysis system) of a two-dimensional textile according to the present disclosure, at a higher magnification than for FIG. 4A, the textile being knitted with multifilaments of PET and then coated three times with a 50/50 CXN/chitosan mixture.

FIGS. 5A and 5B represent scanning electron microscopy images of such three-dimensional meshes.

Preparation of Textile Reinforcement Member Based on Oxidized Collagen/Chitosan Mixture Two-dimensional meshes made of oxidized collagen/chitosan mixture were knitted from the yarn obtained by the process described in the Example 5.

Preparation of Calendered Collagen Porous Layer

A collagen/chitosan mixture was prepared by mixing an acidic solution of oxidized collagen and an acidic solution of chitosan with respectively 30% and 70% composition in mass. The acidic solution of chitosan is composed of two different degree of acetylation of 2.5% and 26% in the respectively proportions of 30% and 70%. The final polymer concentration is about 1% (w/w).

The blend of oxidized collagen and chitosan (approximately 121 g) were poured within a 12 cm by 7 cm plastic box and freeze-dried for 24 hours. The samples were then neutralized in a 20% ammonia bath for 1 hour and thoroughly washed in deionized water until the pH reached 7.

The freeze-dried sponges were then calendered to obtain a material with a final thickness of 0.13 mm.

Preparation of Collagen Non-Porous Layer

To a 3.9% oxidized collagen solution, an ultra-filtered concentration of solution of PEG 4000 (polyethylene glycol having a molecular weight of 4000 g/mol) and glycerol was added in order to achieve a PEG concentration of 1% and a glycerol concentration of 0.6%.

The pH of the suspension was adjusted to 7.0 by adding concentrate sodium hydroxide solution.

The volume of the solution was adjusted with sterile water to obtain a final concentration of collagen, chitosan, PEG, and glycerol of 2.7%, 0.55%, 0.9%, and 0.54% respectively.

The oxidized collagen solution was then poured into a thin layer on a flat hydrophobic support of PVC or polystyrene, with a density of 0.133 g solution/cm$^2$.

The layer is then exposed to a sterile stream of air at ambient temperature leading to complete evaporation in approximately 18 hours.

Assembly of a Three-Layer Dural Implant without Textile

A thin layer of an oxidized collagen solution was poured on a flat hydrophobic support of PVC or polystyrene, with a density of 0.400 g solution/cm$^2$.

The surfaces were then exposed to a sterile stream of air at ambient temperature for less than one hour.

A calendered sponge was then gently applied on the gelling layer of the oxidized collagen and the two layers were exposed to a sterile stream of air at ambient temperature overnight.

A second layer of oxidized collagen solution was then distributed on the bi-layer composite with a reduced density of 0.133 g solution/cm$^2$.

The three layers composite was then exposed to a sterile stream of air at ambient temperature, leading to complete evaporation in approximately 18 hours.

The composite material was then sterilized by gamma radiation.

Assembly of a Three-Layer Dural Implant with PLA or Oxidized Collagen/Chitosan Textile A thin layer of an oxidized collagen solution was poured on a flat hydrophobic support of PVC or polystyrene, with a density of 0.400 g solution/cm$^2$.

A textile reinforcement member (based on PLA or oxidized collagen/chitosan) was then laid over the collagen solution, and pressed into the solution. Additional solution was applied on top of the original volume of solution to ensure the reinforcement member was completely embedded within the solution.

The surfaces were then exposed to a sterile stream of air at ambient temperature for less than one hour.

A calendered sponge was then gently applied on the gelling layer of the oxidized collagen and the two layers were exposed to a sterile stream of air at ambient temperature overnight.

A second layer of oxidized collagen solution was then distributed on the bi-layer composite with a reduced density of 0.133 g solution/cm$^2$.

The three layers composite was then exposed to a sterile stream of air at ambient temperature, leading to complete evaporation in approximately 18 hours.

The composite material was then sterilized by gamma radiation.

Figure 3:
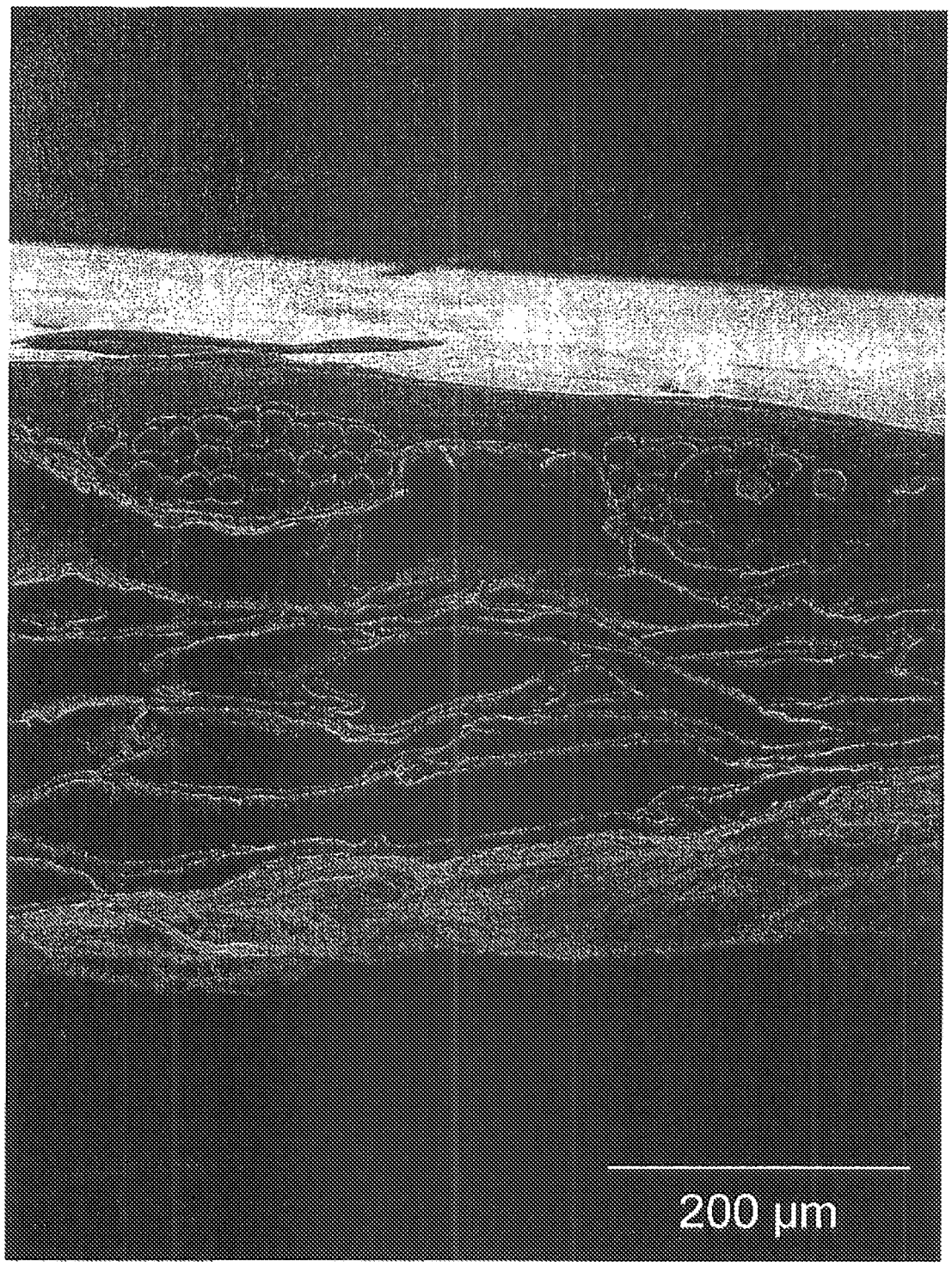
FIG. 3 represents a scanning electron microscopy image (Hitachi S800 scanning electron microscope with image acquisition and analysis system) of a multilayer implant according to the present disclosure, including a textile made from polylactic acid (PLA), from a side view.
Figure 4A:
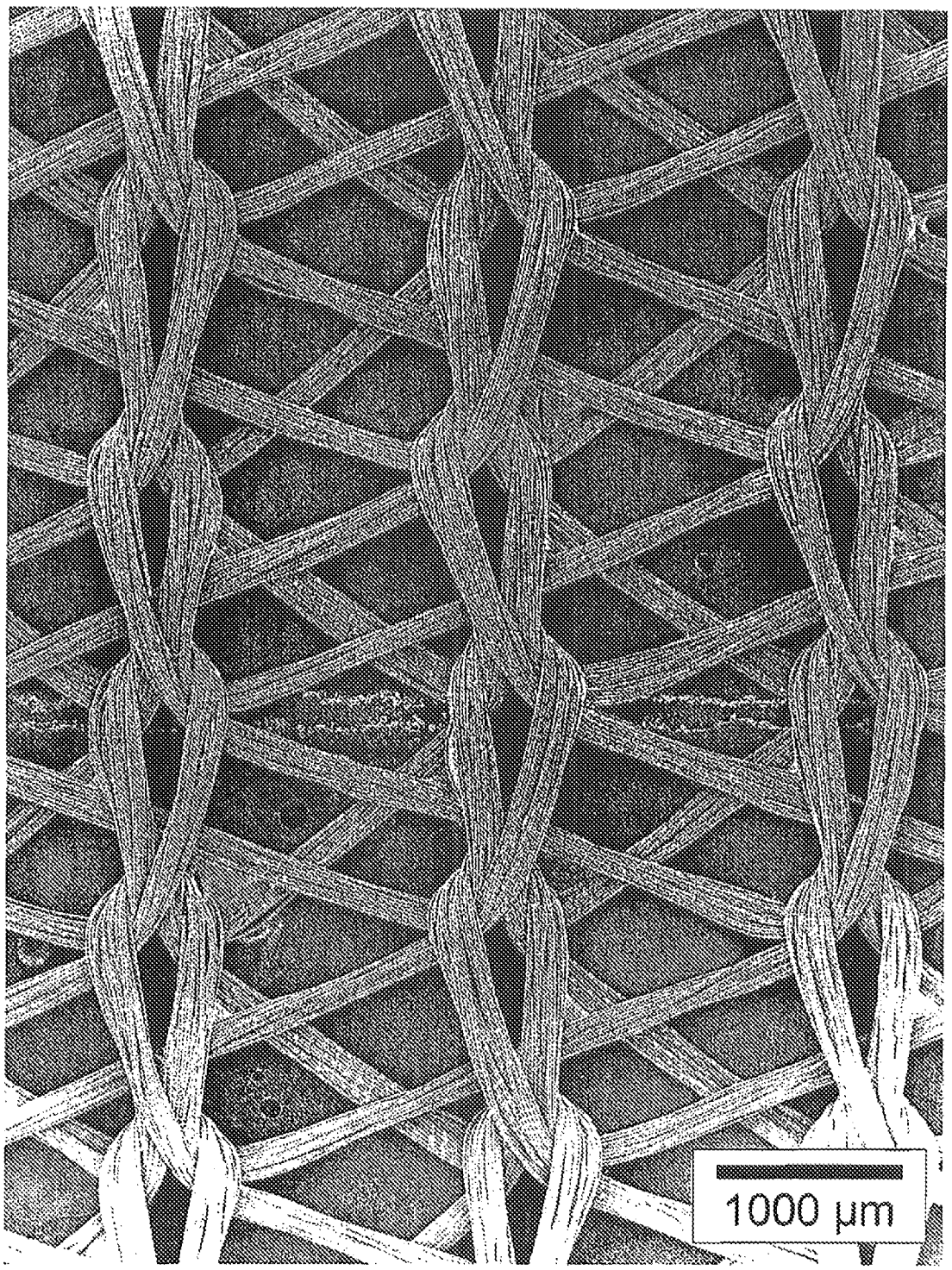
FIG. 4A represents a scanning electron microscopy images (Hitachi S800 scanning electron microscope with image acquisition and analysis system) of a two-dimensional textile according to the present disclosure, the textile being knitted with multifilaments of PLA and then coated three times with a 50/50 CXN/chitosan mixture.
Figure 4B:
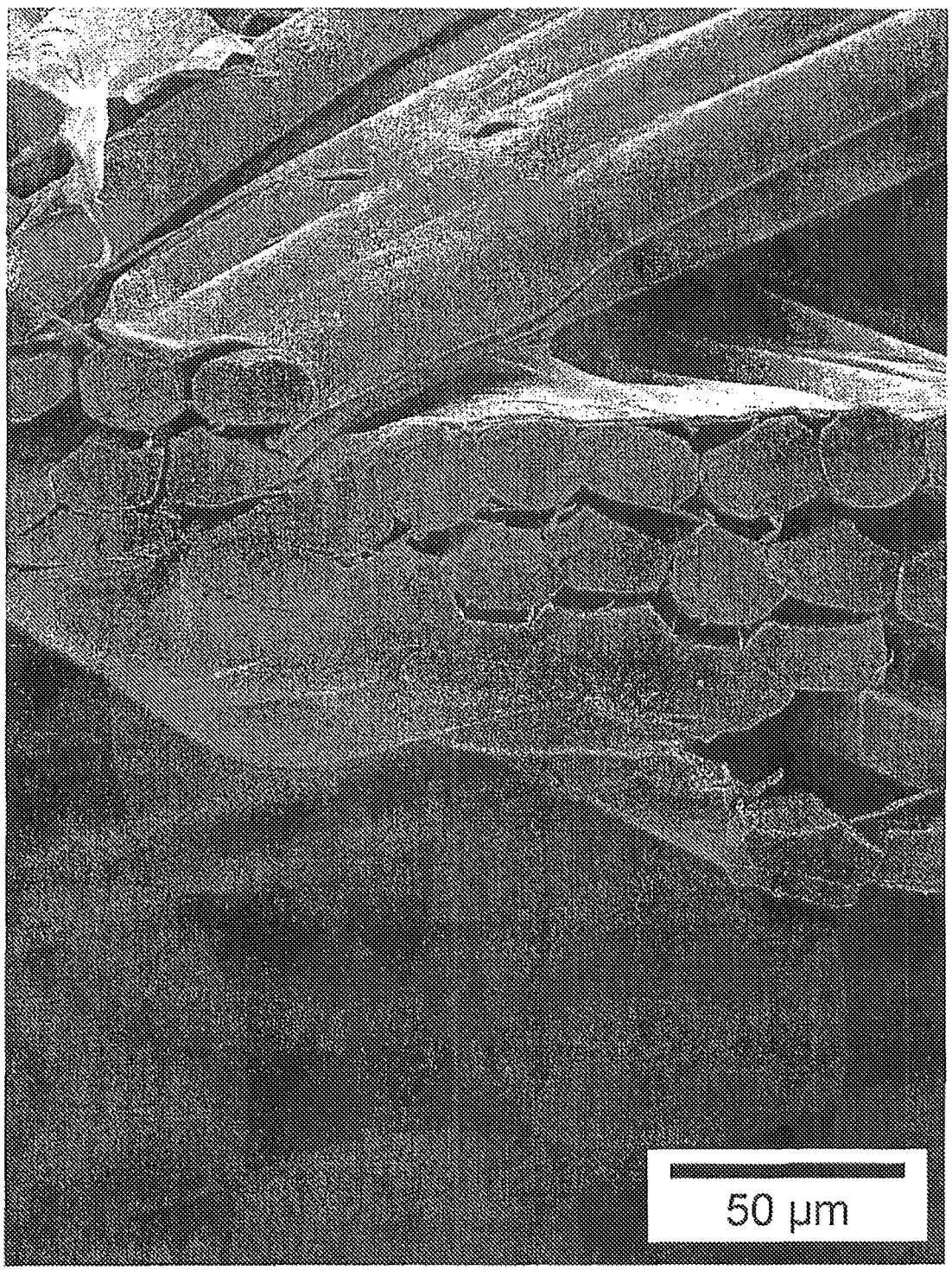
FIG. 4B represents a scanning electron microscopy images (Hitachi S800 scanning electron microscope with image acquisition and analysis system) of a two-dimensional textile according to the present disclosure, at a higher magnification than for FIG. 4A, the textile being knitted with multifilaments of PLA and then coated three times with a 50/50 CXN/chitosan mixture.

FIG. 3 represents a scanning electron microscopy image of such a multilayer implant.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A compound comprising a functionalized collagen covalently bonded directly to chitosan without the use of a crosslinking agent, wherein the chitosan has a degree of acetylation from about 35 to 50% and wherein the collagen is functionalized by oxidative cleavage.

2. A compound as in claim 1 wherein the functionalized collagen includes one or more reactive moieties selected from the group consisting of aldehydes, sulfones, vinylsulfones, isocyanates, and acid anhydrides.

3. The compound of claim 1 wherein the functionalized collagen includes one or more reactive moieties selected from the group consisting of —$CO_2N(COCH_2)_2$, —$CO_2N(COCH_2)_2$, —$CO_2H$, —$CHO$, —$CHOCH_2$, —$N=C=O$, —$SO_2CH=CH_2$, —$N(COCH)_2$, and —$S$—$S$—$(C_5H_4N)$.

4. The compound of claim 1 wherein the functionalized collagen is covalently bonded to at least a second chitosan with a degree of acetylation selected from about 0.5 to 60%.

5. An implant comprising a compound containing a functionalized collagen covalently bonded directly to chitosan without the use of a crosslinking agent, wherein the chitosan has a degree of acetylation from about 35 to 50% and wherein the collagen is functionalized by oxidative cleavage.

6. The implant of claim 5 comprising a sponge containing said compound.

7. The implant of claim 5 comprising a textile containing said compound.

8. The implant of claim 5 comprising a hydrogel containing said compound.

9. The implant of claim 5 comprising threads containing said compound.

10. The implant of claim 5 comprising a non knitted, non woven composite containing said compound.

11. The implant of claim 5 comprising a film containing said compound.

12. The implant of claim 5 comprising a mesh coated with a composition containing said compound.

13. A method of forming a bioresorbable compound comprising contacting a functionalized collagen with a glycosaminoglycan without the use of a crosslinking agent, wherein the glycosaminoglycan is chitosan having a degree of acetylation from about 35% to 50% and wherein the collagen is functionalized by oxidative cleavage, wherein a deionized water solution of functionalized collagen is combined to a deionized water solution of chitosan having a degree of acetylation from about 35% to 50% to allow the functionalized collagen to mix with the chitosan and form said compound.

14. The method of claim 13, wherein the pH of the solution of functionalized collagen is adjusted between 2 and 7.5.

15. The method of claim 13, wherein the pH of the solution of glycosaminoglycan is adjusted between 2 and 7.5.

16. The method of claim 14, wherein the pH of the solution of glycosaminoglycan is adjusted between 2 and 7.5.

* * * * *